(12) United States Patent
Buthe et al.

(10) Patent No.: US 8,758,730 B2
(45) Date of Patent: Jun. 24, 2014

(54) COMPOSITIONS, USE AND METHOD FOR THE USE OF SURFACE ACTIVE PROTEINS IN TOPICAL DRUG DELIVERY ACROSS KERATIN

(75) Inventors: Andreas Buthe, Steinfurt (DE);
Andreas Hafner, Gelterkinden (CH);
Franz Kaufmann, Freiburg (DE);
Babette Fiedler, Darmstadt (DE);
Guido Meurer, Seeheim-Jugenheim (DE); Gordon Bradley, Liestal (CH)

(73) Assignee: B.R.A.I.N. Biotechnology Research and Information Network AG, Zwingenberg (DE)

( * ) Notice: Subject to any disclaimer, the term of this patent is extended or adjusted under 35 U.S.C. 154(b) by 176 days.

(21) Appl. No.: 13/202,112

(22) PCT Filed: Feb. 19, 2010

(86) PCT No.: PCT/EP2010/052125
§ 371 (c)(1),
(2), (4) Date: Oct. 17, 2011

(87) PCT Pub. No.: WO2010/097344
PCT Pub. Date: Sep. 2, 2010

(65) Prior Publication Data
US 2012/0058199 A1 Mar. 8, 2012

(30) Foreign Application Priority Data
Feb. 26, 2009 (EP) .................................... 09153770

(51) Int. Cl.
*A61K 47/42* (2006.01)
*A61Q 3/00* (2006.01)

(52) U.S. Cl.
USPC ............................. 424/61; 514/20.7; 514/773

(58) Field of Classification Search
None
See application file for complete search history.

(56) References Cited

U.S. PATENT DOCUMENTS

| 5,037,632 | A | * | 8/1991 | Gross et al. ..................... 424/47 |
| 5,972,317 | A | | 10/1999 | Sorenson et al. |
| 6,517,863 | B1 | * | 2/2003 | LaTorre et al. ............... 424/447 |
| 2003/0217419 | A1 | | 11/2003 | Vic |
| 2009/0041922 | A1 | | 2/2009 | Kuhnle et al. |
| 2009/0136433 | A1 | | 5/2009 | Subkowski et al. |
| 2010/0166627 | A1 | | 7/2010 | Baus et al. |
| 2010/0170142 | A1 | | 7/2010 | Posselt et al. |
| 2010/0240774 | A1 | | 9/2010 | Subkowski |
| 2011/0159050 | A1 | | 6/2011 | Hafner et al. |

FOREIGN PATENT DOCUMENTS

| JP | 10-226639 A | 8/1998 |
| JP | 2004505928 A | 2/2004 |
| WO | 2004/000880 A1 | 12/2003 |
| WO | 2006136607 A | 12/2006 |
| WO | 2007042682 A1 | 4/2007 |
| WO | 2009/037061 A | 3/2009 |

OTHER PUBLICATIONS

Copending U.S. Appl. No. 11/887,282, filed Aug. 17, 2007.
Copending U.S. Appl. No. 13/130,128, filed May 19, 2011.
Askolin et al., Biomacromolecules, ACS, vol. 7, No. 4, (Apr. 2006) pp. 1295-1301.
Schreier et al., Biochimica et Biophysica Acta, vol. 1508, No. 1-2 (Nov. 2000) pp. 210-234.
Plank et al., Advanced Drug Delivery Reviews, vol. 34, No. 1, (Jan. 1998) pp. 21-35.
Mohorcic et al., International Journal of Pharmaceutics vol. 332, No. 1-2 (Mar. 2007) pp. 196-201.

\* cited by examiner

*Primary Examiner* — Jeffrey E Russel
(74) *Attorney, Agent, or Firm* — Pillsbury Winthrop Shaw Pittman LLP

(57) ABSTRACT

The present invention provides the use of surface active proteins, especially class I and class II hydrophobins, in topically applied pharmaceutical formulations. The invention is particularly directed to topically applied pharmaceutical products for enhancing the penetration to achieve a transungual delivery of a prophylactically and/or therapeutically effective amount of an active ingredient (drug) to a patient (including animals and humans) into and/or through a nail, of the animal or human body, in order to treat one or more of a variety of diseases or disorders. Related embodiments of the invention are also disclosed.

10 Claims, 3 Drawing Sheets

COMPOSITIONS, USE AND METHOD FOR THE USE OF SURFACE ACTIVE PROTEINS IN TOPICAL DRUG DELIVERY ACROSS KERATIN

FIELD OF INVENTION

The present invention provides the use of (especially highly) surface active proteins in topically applied pharmaceutical formulations. The invention is particularly directed to topically applied pharmaceutical products for enhancing the penetration to achieve a transungual delivery of a prophylactically and/or therapeutically effective amount of an active ingredient (drug) to a patient (including animals and humans) into and/or through the keratinized surface of a nail, of the animal or human body, in order to treat one or more of a variety of diseases or disorders.

BACKGROUND OF THE INVENTION

Hydrophobins are a class of surface active proteins with approximately 100 to 150 amino acids. Self-assembly of hydrophobins is accompanied by conformational changes. Monomeric class I and class II hydrophobins are rich in [beta]-sheet structure. The hydrophobins are characteristic of filamentous fungi, for example of *Schizophyllum commune* or *Trichoderma reesei*. Up to now they have, inter alia, been described to form stable layers on surfaces that would be expected to inhibit the penetration or work as deposit matrix (binding the active ingredients to surfaces e.g. of materials and thus immobilizing it e.g. on hair or the like). This has been described (see e.g. WO 2004/000880). Also cosmetic compositions allowing the treatment of materials containing keratin, mucous membranes and teeth have been described, but again here the asserted mode of action relates merely to the high affinity of hydrophobins to keratinic surfaces of the human body, such as hair, skin and nails (WO 2006/136607) and their anchoring effect to any active or other ingredients for enhancing the concentration of the ingredients at the surface, allowing for a targeting to and a long duration of the effects on the surface of the keratin. Moisture addition and skin soothing properties or colouring are in the foreground here. No penetration dependent pharmaceutical effects are described or suggested. Especially, no examples showing an enhanced activity are provided—in fact the approach appears counter-intuitive as the improved binding should result in less free active ingredient being available at places where it is required, especially if treatment inside or below a keratinic layer is desired. This is also confirmed by US 2003/0217419 where it is described that on hair hydrophobin allows to obtain a cosmetic deposit that withstands several shampoo washes.

In many cases it would be desirable to improve the penetration of drugs (active ingredients) into and/or through keratinized surfaces of patient bodies, especially nail, so that pharmaceutically effective concentrations can be achieved at the required site.

GENERAL DESCRIPTION OF THE INVENTION

It has now, however, surprisingly been found that in fact surface active proteins, such as the hydrophobins, can be used as penetration enhancers for active ingredients through nail surfaces of the animal or human body.

The present invention, therefore, in a first embodiment relates to the use of a surface active protein as penetration enhancer allowing to achieve a transungual delivery of a prophylactically or (especially) therapeutically effective amount of at least one active ingredient to a patient (including animals and humans) into and/or through the keratinized surface of said patient, said use comprising (preferably consisting in) admixing said surface active protein to a pharmaceutical formulation further comprising one or more active ingredients.

In a second embodiment, the invention relates to the use of a surface active protein for the preparation of a pharmaceutical formulation for the treatment of a disease in a patient at a position that requires direct contact with an active ingredient, where the surface active protein works as a penetration enhancer to allow to achieve a transungual delivery of a prophylactically or (especially) therapeutically effective amount of at least one active ingredient to a patient (including animals and humans) into and/or through a keratinized surface including nails of said patient.

In a third embodiment, the invention relates to a method of using a surface active protein as penetration enhancer to achieve a transungual delivery of a prophylactically or (especially) therapeutically effective amount of at least one active ingredient to a patient (including animals and humans), especially in need of such treatment, into and/or through a keratinized surface including nails of said patient, said use comprising admixing said surface active protein to a pharmaceutical formulation together with one or more active ingredients and optionally one or more pharmaceutically acceptable carriers and/or ingredients.

In a fourth embodiment, the invention related to a method of enhancing the penetration of at least one active ingredient to a patient into and/or through a keratinized surface including nails of said patient, to achieve a transungual delivery of a prophylactically or (especially) therapeutically effective amount of said at least one active ingredient, said use comprising admixing said surface active protein to a pharmaceutical formulation together with one or more active ingredients and optionally one or more pharmaceutically acceptable carriers and/or ingredients, and topically administering the resulting pharmaceutical formulation to said patient.

In a fifth embodiment, the invention relates to a pharmaceutical formulation, comprising at least one pharmaceutically active ingredient and a penetration enhancer in the form of a surface active protein especially for use in a patient less or not treatable without penetration enhancer, comprising increasing delivery of said active ingredient(s) into and/or through a nail, together with at least one further pharmaceutically acceptable carrier.

The first to fifth embodiment mentioned above, and also particular (e.g. preferred) embodiments thereof, are also referred to herein as pharmaceutical formulations of the invention or made or used according to the invention, or as pharmaceutical formulations, their use or their manufacture.

The pharmaceutical formulations, which are to be topically applied, of the invention or made or used according to the invention comprise among others (a) at least on (pharmacologically) active ingredient and (b) a non-irritating permeation enhancer.

This invention is particularly directed to such topically applied pharmaceutical formulations, their use or their manufacture, for the enhanced delivery of a therapeutically effective amount of an active ingredient across the keratinized surface of the animal or human body including nails (or hoofs); and further across membranes below such keratinized surfaces, membranes of body cavities, and optionally into body tissues, organs and/or systems in proximity to any of the foregoing.

In one specific embodiment, this invention is directed to such topically applied pharmaceutical formulations, their manufacture or their use, for the enhanced delivery of a prophylactically or (especially) therapeutically effective amount of at least one active ingredient to a diseased or infected nail bed, nail matrix, and/or nail plate in the toenails and/or fingernails of a patient, wherein the disease or infection is an infectious disease, especially a fungal disease, more especially onychomycosis; or inflammation, cancer, infection or degeneration.

DETAILED DESCRIPTION OF THE INVENTION

The general terms, symbols and expression preferably have the meanings given in the following definitions which may replace one, two or more or all of the more general expressions used in the present disclosure to define specific embodiments (aspects) of the invention which are examples for preferred embodiments:

The nail, derived from the epidermis, is composed mostly of highly disulfide-linked keratin and is approximately 100 times thicker than the stratum corneum, thereby providing an even more daunting barrier to medication delivery. However, water permeation rate of the nail is around ten times higher than that of the stratum corneum. On the other hand, the nail contains much less water than the stratum corneum of the skin.

Onychomycosis is a fungal infection of the nail plate and bed of the fingernails or toenails and is responsible for up to 50% of nail disorders. The prevalence of onychomycosis is about 6-8% in the adult population. In all forms of onychomycosis, the nail becomes variously disfigured and distorted. Onychomycosis is caused by 3 main classes of fungi: dermatophytes, yeasts, and nondermatophyte molds and is one of the most difficult fungal infections to treat. The lengthy period the nail takes to grow, the hardness of the nail plate, and location of the infectious process between the nail bed and plate are major factors interfering with the eradication of fungal agents affecting these tissues. Treatment of onychomycosis is usually using topical antifungal agents or oral therapy. Oral therapy has side effects such as liver toxicity, while topical therapy is limited by the low permeability of the nail plate. Topical drug delivery to nails may be via ointments, creams, lotions, gels, sprays, plasters, patches, bandages and the like.

Targeting drug treatment of onychomycosis is challenging because the infection is embedded within the nail and is difficult to reach due to the highly restrictive barrier of the human nail. The nail plate behaves as a hydrophilic gel membrane and is the main barrier to permeation of topical drugs, limiting the effectiveness of this treatment type. In order to deliver a sufficient amount of drug into the nail plate, the permeability of the nail plate to the drug must be enhanced.

The chemical composition of nail and experimental evidence suggest that the aqueous pathway plays a dominant role in drug penetration into nail. Water appears to be the principal plasticizer for the nail. Upon being hydrated, hard nail plates become softer and more flexible. Nail hydration is influenced by many factors, such as solution pH and certain chemicals.

A serious challenge to the formulation of a topically applied pharmaceutical composition is ensuring that it is biocompatible with the tissues to which it is to be applied such that the tissues will not be damaged or irritated by the formulation, or by its components. This is particularly challenging since many topical excipients that are known to be permeation enhancers are also known to be skin and membrane irritants. In general, penetration enhancers can be divided into two large groups (see: Current medicinal chemistry ISSN 0929-8673: 2005, vol. 12, no19, pp. 2273-2291):

(i) small polar solvents, e.g. ethanol, propylene glycol, dimethylsulfoxide, and (ii) amphiphilic compounds containing a polar head and a hydrophobic chain, e.g. fatty acids and alcohols, 1-dodecylazepan-2-one (Azone), 2-nonyl-1,3-dioxolane (SEPA 009), and dodecyl-2-dimethylaminopropanoate (DDAIP). Amphiphilic compounds are also known to adsorb on a keratin surface and can be utilized in hair treatments.

Low boiling solvents such as ethanol have only temporary activity as penetrators as they quickly evaporate from the affected nail surfaces. Polar solvents can also be irritants and can damage the nail plate. Such penetration enhancers may be used in combination with chemical modifiers of the nail keratin matrix such as:

(a) Keratolytic agents, such as urea and salicylic acid are often used to soften nail plates.

Examples include salicylic acid, urea, and guanidine hydrochloride—such substances which may disrupt the tertiary structure, and possibly secondary linkages (such as hydrogen bonds) in keratin, thus promoting penetration through the nail.

(b) Sulphur containing compounds such as mercaptan compounds, sulfites and bisulfites, which act by disrupting the disulfide bridges in keratin;

(c) Surfactants, primarily of the anionic type, are known to be able to interact with keratin.

The disadvantage of using enhancers that change the chemistry or the physical internal environment of the nail plate is that cause it may cause permanent damage i.e. the process is non-reversible.

Similar issues exist regarding the delivery of drugs into and through skin, which also includes a keratinized surface.

Within the scope of the current inventions, topical delivery of the pharmaceutical formulations containing the claimed surface active protein that enhance penetration (that is, active as penetration enhancers) can be applied by spraying or via patches and by ointments, creams, lotions, gels, sprays, plasters, bandages, and the like.

A specific embodiment covered by this invention are anti-inflammatory pharmaceutical formulations applied and their use or manufacture according to the invention. Anti-inflammatory drugs are drugs with analgesic, antipyretic and, in higher doses, anti-inflammatory effects—they reduce pain, fever and inflammation. Topical anti-inflammatory drugs are effective in the relief of pain caused by soft tissue injury, sprains, strains and trauma. Ketoprofen, felbinac, ibuprofen and piroxicam are examples which have proven efficacy, as well as others mentioned below.

Penetration enhancers may also help to overcome the barrier properties of the skin or mucosal surfaces and facilitate the percutaneous absorption of an active agent added to the pharmaceutical formulations. Alternative names for penetration enhancers exist such as permeation enhancers, sorption promoters and accelerants.

Skin models are frequently used to test skin irritating effects of substances as well as skin absorption and/or penetration. A comparison of different skin models with excised human and animal skin (Schmook et al. 2001, Comparison of human skin or epidermis models with human and animal skin in in-vitro percutaneous absorption, Int. J. Pharmaceutics 215, 51-56) showed that, depending on the compound used for penetration studies, skin equivalents can provide a penetration barrier which is sufficient to study permeation rates and their modulation by penetration enhancers.

Penetration enhancers can interact with molecules in the stratum corneum to modify its permeability to achieve delivery at therapeutically effective rates. Such permeation enhancers can be applied to the skin by pretreatment or concomitantly or jointly with the drug. However, incorporation of penetration enhancers into products has been mitigated by safety concerns related to the health of the skin membrane. Accordingly, overcoming the keratinic barrier in a safe and effective way still remains the bottleneck of transdermal and especially transungual topical therapies.

Some useful permeation enhancers include non-ionic surfactants, one or more can be selected from the group including glyceryl mono-oleate, glyceryl mono-laurate, sorbitan mono-oleate, glyceryl tri-oleate, and isopropyl myristate. For an early list of known penetration agents (see "Pharmaceutical Skin Penetration Enhancement", Marcel Dekker, New York 1993, pages 229-24). WO 2006/103638 A2 describes non-ionic surfactants as excipients in a topical formulation of terbinafine and U.S. Pat. No. 6,455,592 discloses a hydrophilic penetration agent, namely dipropylene glycol dimethyl ether, to enhance the penetration of antifungal agents through the nails.

Penetration enhancers as substances used in pharmaceutical preparation have to meet a set of qualitative criteria. They must not be: toxic; irritate, allergic or sensitized to the skin; and they should be pharmacologically inert at the concentration required to exert adequate permeation action; their effect should be immediate, predictive and reversible; and they should be readily incorporated into pharmaceutical preparations. Most of the chemicals studied are either toxic or too irritating for use on human skin.

The present invention thus further provides the co-delivery and combining of drug having a low rate of permeation and a surface active protein to enhance the penetration of an active ingredient (drug).

A surface active protein is preferably a protein with amphiphilic properties, especially a protein that is capable of forming layers on (especially hydrophobic or hydrophilic) surfaces. Among the possible proteins, proteins like latherin from horse sweat (see e.g. J. G. Bealey et al., Biochem J. 1986 May 1; 235(3): 645-650, Phospholipase C, amyloid or amyloid-like proteins, such as amyloid-β, β-casein, the bioemulsifier of *Acinetobacter radioresistens* KA53, referred to as alasan, SapB from *S. coelicolor* A3(2) and *S. tendae*, glykolipid transfer protein, chaplines (Claassen et al., Genes Dev. 1714-1726, 2003; Elliot et al., Genes Dev. 17, 1727-1740) or in a specific embodiment of the invention proteins from the class commonly referred to as hydrophobins, especially hydrophobins class 1 and/or class 2.

Hydrophobins are small fungal surface active proteins that self-assemble at interfaces into films with nanoscale structures. A potential use of surface active proteins, preferably hydrophobins, as penetration enhancers for the topical application of drugs has not been described before.

It will be understood that it is also possible to use a mixture of a plurality of different hydro-phobins according to the invention.

In the context of the invention, the term "hydrophobins" hereinbelow is especially to be understood as polypeptides of the general structural formula (I)

$$X_n\text{-}C^1\text{-}X_{1\text{-}50}\text{-}C^2\text{-}X_{0\text{-}5}\text{-}C^3\text{-}X_{1\text{-}100}\text{-}C^4\text{-}X_{1\text{-}100}\text{-}C^5\text{-}X_{1\text{-}50}\text{-}C^6\text{-}X_{0\text{-}5}\text{-}C^7\text{-}X_{1\text{-}50}\text{-}C^8\text{-}X_m \quad \text{(I)},$$

wherein X can be any of the 20 naturally occurring amino acids (Phe, Leu, Ser, Tyr, Cys, Trp, Pro, His, Gln, Arg, Ile, Met, Thr, Asn, Lys, Val, Ala, Asp, Glu, Gly). The Xs therein can be the same or different. The indices adjacent to X in each case indicate the number of amino acids, C is cysteine, alanine, serine, glycine, methionine or threonine, at least four of the ami-no acids ($C^1$-$C^8$) designated by C being cysteine, and the indices n and m, each indepen-dently of the other, are natural numbers from 0 to 500, preferably from 15 to 300. Those sub-stances and the preparation thereof are known, for example from the literature mentioned at the outset, such as, for example, WO 06/103230 or WO 2006/136607, which are included by reference here especially regarding the disclosure of hydrophobins.

The amino acids designated $C^1$ to $C^8$ are preferably cysteines, but they can also be replaced by other amino acids of similar steric structure, preferably by alanine, serine, threonine, methionine or glycine. In any event at least 4, preferably at least 5, especially at least 6 and more especially at least 7 of the positions $C^1$ to $C^8$ are to consist of cysteines. In the proteins according to the invention, cysteines can either be present in reduced form or can form di-sulfide bridges with one another. Special preference is given to the intramolecular formation of bridges, especially those having at least 1, preferably 2, especially preferably 3 and more especially preferably 4 intramolecular disulfide bridges. In the case of the above-described replacement of cysteines by amino acids of similar steric structure, the C positions that are capable of forming intramolecular disulfide bridges with one another are advantageously replaced pairwisely.

When cysteines, serines, alanines, glycines, methionines or threonines are also used in the positions indicated by X, the numbering of the individual C positions in the general formulae can change accordingly.

For carrying out the present invention, preference is given to the use of hydrophobins of the general formula (II)

$$X_n\text{-}C^1\text{-}X_{3\text{-}25}\text{-}C^2\text{-}X_{0\text{-}2}\text{-}C^3\text{-}X_{5\text{-}50}\text{-}C^4\text{-}X_{2\text{-}35}\text{-}C^5\text{-}X_{2\text{-}15}\text{-}C^6\text{-}X_{0\text{-}2}\text{-}C^7\text{-}X_{3\text{-}35}\text{-}C^8\text{-}X_m \quad \text{(II)},$$

wherein X, C and the indices adjacent to X are as defined hereinabove, the indices n and m are numbers from 0 to 300, and the proteins are furthermore distinguished by the above-mentioned change in contact angle.

Special preference is given to the use of hydrophobins of the general formula (III)

$$X_n\text{-}C^1\text{-}X_{5\text{-}9}\text{-}C^2\text{-}C^3\text{-}X_{11\text{-}39}\text{-}C^4\text{-}X_{2\text{-}23}\text{-}C^5\text{-}X_{5\text{-}9}\text{-}C^6\text{-}C^7\text{-}X_{6\text{-}18}\text{-}C^8\text{-}X_m \quad \text{(III)},$$

wherein X, C and the indices adjacent to X are as defined hereinabove, the indices n and m are numbers from 0 to 200, and the proteins are furthermore distinguished by the above-mentioned change in contact angle and, further, at least 6 of the amino acids designated by C are cysteine. Especially preferably, all amino acids C are cysteine.

The residues Xn and Xm can be peptide sequences that are also naturally linked to a hydrophobin. One or two of the residues, however, can also be peptide sequences that are not naturally linked to a hydrophobin. Those include also the residues Xn and/or Xm in which a peptide sequence occurring naturally in a hydrophobin has been lengthened by a peptide sequence that does not occur naturally in a hydrophobin.

An example is H*A (His-tagged hydrophobin DewA fused to the solubility tag Yaad, supplied by BASF; for production see WO 2006/082251).

The proteins used in accordance with the invention can also, in addition, be modified in their polypeptide sequence, for example by glycosylation, acylation (e.g. acetylation) or by chemical cross-linking, for example, with glutaric dialdehyde.

A property of the proteins used in accordance with the invention is the change in surface properties when the surfaces are coated with the proteins. The change in surface properties can be determined experimentally by measuring the contact angle of a water droplet before and after a surface has been coated with the protein and ascertaining the difference between the two measurements.

The polypeptides according to formula (I) or more any hydrophobins according to the invention are thus furthermore characterized by the property that at room temperature, after coating a glass surface, they bring about an increase in the contact angle of a water droplet usually of at least 20°, in another invention embodiment at least 25°, in another invention em-bodiment at least 30°, and in yet another invention embodiment at least 35°, e.g. 35 to 65°, each by comparison with the contact angle of a water droplet of the same size with the glass surface uncoated. The procedure for taking contact angle measurements is known to the person skilled in the art. For example, the contact angle may be determined on glass (window glass from Sueddeutsche Glas, Mannheim, Germany), using a concentration of 100 µg/ml of the hydrophobin to be tested, incubation of the glass plates overnight at 80° C. in 50 ml sodium acetate pH 4 with 0.1% Tween 20 in water, washing after the covering in distilled water, then incubation for 10 min at 80° C. in a 1% sodium dodecylsulfate solution in distilled water, followed by washing with distilled water. The samples are dried in air and the contact angle (in degree) of a drop or 50 µl is determined. The contact angle measurement is made on a Dataphysics Contact Angle System OA 15+, Software SCA20.2.0 (November 2002) according to the manufacturers instructions.

Suitable hydrophobins for the implementation of the present invention are, for example, those of WO 06/103230 or WO 2006/136607 which especially regarding their disclosure of hydrophobins are incorporated here by reference. They can also be only parts or derivatives thereof. It is also possible for a plurality of hydrophobins, preferably 2 or 3, of identical or different structure to be linked to one another and to be linked to a corresponding suitable polypeptide sequence that is not naturally bound to a hydrophobin. Important is that they at least maintain their property of increasing in the contact angle of a water droplet, or more specifically their property to enhance penetration through keratinized surfaces by the methods described in the Examples.

The preparation of hydrophobins can also be carried out by genetic engineering methods (recombinantly) in which a nucleic acid sequence, especially a DNA sequence, coding for the hydrophobin in the context of this invention is so inserted into a host organism that the desired protein is produced by gene expression of the nucleic acid sequence. The gene expression can be carried out either in a heterologous or in a homologous host strain. Such methods are known in principle to the person skilled in the art and are disclosed, for example, in WO 06/082251.

This allows to produce recombinant hydrophobins.

Suitable host organisms (production organisms) for the said method of preparation can be prokaryotes (including the Archaea) or eukaryotes, especially bacteria including halobacteria and methanococci, fungi, insect cells, plant cells and mammalian cells, especially preferably *Escherichia coli, Bacillus subtilis, Bacillus megaterium, Aspergillus oryzea, Aspergillus nidulans, Aspergillus niger, Pichia pastoris, Pseudomonas* spec., *lactobacilli, Hansenula polymorpha, Trichoderma reesei*, SF9 (and related cells), among others.

The proteins produced can either be used directly in the form of fusion proteins or, after splitting off and removing the fusion partner, used in the form of "pure" hydrophobins.

The hydrophobins can also be obtained in glycosylated or acylated or other modified form by genetic engineering methods, using appropriate host systems (e.g. of eukaryotic origin).

Alternatively or in addition, naturally occurring hydrophobins can be isolated from natural sources by suitable methods. Reference is made by way of example to Wösten et. al., Eur. J. Cell Bio. 63, 122-129 (1994) or WO 96/41882.

Among the hydrophobins isolated from natural sources, those belonging to class I, such as CFTH1, SC4, ABH3, EAS, or (in a specific embodiment) SC3 from *Schizophyllum commune* or HBF II from *Trichoderma reesei* (new name: *Hypocrea jecorina*), may be mentioned, as well as those belonging to class II, such as HFBII, *T. reesei* (accession P79073 [GenBank]); HFBI, *T. reesei* (accession P52754 [GenBank]); SRHI, *Trichoderma harzianum* (accession Y11841 [GenBank]); QID3, *Trichoderma harzianum* (accession P52755 [GenBank]); TR11, TR12, and TR13, the three segments of TH1 *Claviceps fusiformis* (accession Q9UVI4); CPPHI_1, CPPH1_2, CPPH_3, CPPH_4, and CPPH_5, the five segments of cpph1 *Claviceps purpurea* (accession AJ418045 [GenBank]); CRYPA, *Cryparin Cryphonectria parasitica* (accession P52753 [GenBank]); CU, Cerato-ulmin *Ophiostoma ulmi* (accession Q06153 [GenBank]); MAG, Magnaporin *Magnaporthe grisea* (accession AF126872 [GenBank]); HCF5, *Cladosporium fulvum* AJ133703 [GenBank]; HCF6, *C. fulvum* (accession CAC27408 [GenBank] (see e.g. Wosten, Han A. B.: Hydrophobins: Multipurpose Proteins, Annual Review of Microbiology, Publication Date: 1 Jan. 01; Wessels J. G. H. (1994) Annu. Rev. Phytopathol 32:413-437; Wösten H. A. B. (2001) Annu. Rev. Microbiol. 55:625-646; and references mentioned therein, respectively) may be mentioned. For isolation of SC3 see e.g. Wessels, J. G. H. (1997) Advances in Microbial Physiology 38, 1-45; Wösten, H. A. B., de Vries, O. M. H., and Wessels, J. G. H. (1993) Plant Cell 5, 1567-74; Lugones, L. G., Wösten, H. A. B., and Wessels, J. G. H. (1998) Microbiology 144 (Pt 8), 2345-53. For isolation of *Trichoderma reesei* hydrophobin HFBII see Nakari-Setälä, T., Aro, N., Ilmen, M., Kalkkinen, N. and Penttilä, M. 1997, Differential expression of the vegetative and spore-bound hydrophobins of *Tricoderma reesei*, Cloning and characterization of the hfb2 (for HFB22) gene. Eur. J. Biochem. 248, pp. 415-423.

A possible preferred recombinant hydrophobin is H*A (His-tagged hydrophobin DewA fused to the solubility tag Yaad, supplied by BASF; for production see WO 2006/082251).

"Penetration enhancer allowing to achieve a (for example, transdermal, subdermal, transmembrane, musculoskeletal, transungual, transonychial and/or peronychial) delivery of a prophylactically or (especially) therapeutically effective amount of at least one active ingredient" means especially that the presence of the surface active protein leads to a higher concentration of the active ingredient(s) in and/or a higher amount of the active ingredient(s) passing through the keratinized surface per period of time than achieved with an otherwise identical composition without the surface active protein. This can be measured e.g. by the methods described below in the Examples.

"Effective" where used means prophylactically and/or therapeutically, preferably therapeutically active.

Prophylactically effective means especially that the at least one active ingredient prevents or slows the formation of a disease or disorder in comparison to the situation without presence of said at least one active ingredient.

Therapeutically effective means especially that the at least one active ingredient diminishes one or more or all symptoms of a disease or disorder or even leads to partial or complete cure.

Patients can be animals, such as reptiles or birds, or especially mammals, such as humans.

As "keratinized surface", especially nails and the neighbouring skin may be mentioned, more preferably nail. "Nail" includes hoofs in veterinary prophylaxis and treatments.

The at least one active ingredient can, for example, be selected from antibiotics, such as antibacterial (e.g. aminoglycoside antibiotics, such as streptomycine, framycetin, kanamycine of paromycin, cefalosporines, such as cafaloridin, cefodizim, cefoxitin or cefaclor, chloramphenicols, such as fosfomycin, lincomycin antibiotics, such as clindamycin, macrolide antibiotics, such as erythromycin, penicillin antibiotics, such as amoxicillan or ampicillin, polypeptide antibiotics, such as amphomyxin, bacitracin or tyrothricin, glycopeptide antibiotics, such as vancomycin, tetracyclins, such as chlortetracycline, or doxycyclin, steroid antibiotics, such as fusidic acid, or nucleoside antimetabolites), antiviral (e.g. interferones, cyclic amines, such as amantidin, thiosemicarbazones, such as methisazon, biguanides, such as moroxydin, or nucleoside antimetabolites, such as idoxuridin or zidovudin), or (in particular, especially for nail treatment) antifungal agents (antimycotics), e.g. amphotericin B, nystatin, griseofulvin, econazol, miconazol, ketoconazol, clotrimazol, fluconazol, tolnaftat, tolciclat, amorolfin, croconazol, fenticonazol, omoconazol, sertaconazol, naftifin, terbinafin, also undecylen acid (e.g. as Zn salt), salicylic acid, potassium cyanide, phenols, aldehydes, triphenyl methane dyes, sulful, sulfur), e.g. active against onychomycosis of the nail; from antiphlogistics (e.g. non steroidal antiphlogistics or glucocorticoids or the like), anti-rheumatics (such as symptomatic antirheumatics or basis therapeutics) analgesics (especially in the case of treatment of or via skin, such as peripheral analgetics, e.g. aniline derivatives, such as paracetamol, anthranilic acid derivatives, such as flufenaminic acid, mefenaminic acid or nifluminic acid, phenylalkylacid derivatives, such as acemetacin, indomethacin, ibuprofen, felbinac, ketoprofen or naproxen, oxicames, such as tenoxicam or piroxicam, pyrazole derivatives, such as phenazol or metamizol, salicyclic acid derivatives, such as salicyl amide, acetyl salicylic acid or diflunisal), antipyretics and, in particular in higher doses, anti-inflammaory ingredients —which reduce pain, fever and/or inflammation; topical anti-inflammatory drugs are effective in the relief of pain caused by soft tissue injury, sprains, strains and trauma; antipsoriatics, such as glucocorticoids, such as fluticason or mometason, keratolytics, such as salicyclic acid, vitamin D analogs, such as calcipotriol or tacalcitol, methotrexate, retinoids or ciclosporin A, antiproliferative agents, such as antimelanoma agents, e.g. chemotherapeutics or antibodies, respectively, therapeutics or prophylactics against acne, such as retinoids, e.g. alitretinoin, isotretinoin or tretinoin, erythromycin, clindamycin or azelaic acid, tetrycyclins, entiseborrhhids such as antiandrogens, for example cyproteron acetate, or estrogens, such as mestranol, agents against endogenous or exogenous eczema, such as atopic or topic eczema, e.g. antihistaminics, glucocorticoids, benzodiazepines, antiallergics or the like or especially in the case of the eye, agents against cataract or especially conjunctivitis, such as antiallergics.

A position that requires direct contact with an active ingredient can, e.g. in the case of nail, be the nail itself or its immediate surroundings, such as the nail bed, nail matrix, and/or nail plate in the toenails and/or fingernails or, in the case of animals, claws or hoofs, of a patient, or the like.

"In need of treatment" (where the term treatment includes both the prophylactic or the (preferred) therapeutic treatment) in particular means that a patient either prophylactically (e.g. in view of an anticipated or known susceptibility to the outbreak of a disease or disorder) or therapeutically (after the onset of a disease or disorder, e.g. at least one symptom of it) required the treatment to maintain or improve his health condition.

A pharmaceutical formulation used or made according to the invention or as embodiment of the present invention means especially a topical formulation, e.g. in the form of ointments, tinctures, creams (O/W emulsions), rich creams (W/O emulsions), lotions, foams, gels, such as hydrogels or lipogels, pastes, sprays, solid aerosols, shampoos, soaps, plasters, patches, bandages, solutions, emulsions, suspension, and the like, if desired including applications for transdermal systems such as masks, compresses, pads. In fact, any conventional composition that can be applied topically can be utilized in this invention.

In preparing the topical preparations described above, excipients and/or carrier materials including further additives, such as preservatives, thickeners, perfumes and the like customary in the art of pharmaceutical compounding of topical preparation can be used. In addition, conventional antioxidants or mixtures of conventional antioxidants can be incorporated into the topical preparations containing the aforementioned active agent. Among the conventional antioxidants which can be utilized in these preparations are included N-methyl-α-tocopherolamine, tocopherols, butylated hydroxyanisole, butylated hydroxytoluene, ethoxyquin and the like. Cream-base pharmaceutical formulations containing the active agent, used in accordance with this invention, are composed of aqueous emulsions containing a fatty acid alcohol, semi-solid petroleum hydrocarbon, ethylene glycol and an emulsifying agent.

Ointment formulations containing the at least one active agent and a surface active protein in accordance with this invention, for example, comprise admixtures of a semi-solid petroleum hydrocarbon with a solvent dispersion of the active material. Cream compositions containing the active ingredient for use in this invention preferably comprise emulsions formed from a water phase of a humectant, a viscosity stabilizer and water, an oil phase of a fatty acid alcohol, a semi-solid petroleum hydrocarbon and an emulsifying agent and a phase containing the active agent dispersed in a aqueous stabilizer-buffer solution. Stabilizers may be added to the topical preparation. Any conventional stabilizer can be utilized in accordance with this invention. These fatty acid alcohol components function as a stabilizer. These fatty acid alcohol components are derived from the reduction of a long-chain saturated fatty acid containing at least 14 carbon atoms. Also, conventional perfumes and lotions generally utilized in topical preparation for the hair can be utilized in accordance with this invention. Furthermore, if desired, conventional emulsifying agents can be utilized in the topical preparations of this invention. Alternatively gels can be used utilising standard gel carriers.

Creams are oil-in-water emulsions that comprise more than 50% water. As oily base there are used especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example Vaseline® (petrolatum) or paraffin oil. Suitable emulsifiers are surface-active substances having predominantly hydrophilic proper-ties, such as non-ionic emulsifiers, for example fatty acid esters of polyalcohols or ethylene oxide adducts thereof, such as polyglyceric acid fatty acid esters or polyethylene sorbitan fatty acid esters, and also polyoxyethylene fatty alcohol ethers or fatty acid esters, or cor-responding ionic emulsifiers, such as alkali metal salts of fatty alcohol sulfates, for example sodium lauryl sulfate, sodium cetyl sulfate or sodium stearyl sulfate, which are usually used in the presence of fatty alcohols, for example cetyl alcohol or stearyl alcohol. Additives to the aqueous phase are inter alia agents that reduce the drying out of the creams, for example polyalcohols, such as glycerol, sorbitol, propylene glycol and/or polyethylene glycols, also preservatives and perfumes.

Pastes are creams and ointments having secretion-absorbing powder constituents, such as metal oxides, for example titanium oxide or zinc oxide, also talc and/or aluminium silicates, the purpose of which is to bind any moisture or secretions present.

Foams are administered from pressurized containers and are liquid oil-in-water emulsions in aerosol form, there being used as propellants halogenated hydrocarbons, such as chloro-fluoro-lower alkanes, for example dichlorodifluoromethane and dichlorotetrafluoroethane, or preferably non-halogenated gaseous hydrocarbons, air, $N_2O$ or carbon dioxide. As oil phase there are used inter alia the oil phases used above under ointments and creams, likewise the additives mentioned therein.

Tinctures and solutions generally have an aqueous-ethanolic base to which there are, if desired, added inter alia poly-alcohols, for example glycerol, glycols and/or polyethylene glycol, as humectants for reducing evaporation, and fat-restoring substances, such as fatty acid esters with low molecular weight polyethylene glycols, that is to say lipophilic substan-ces that are soluble in the aqueous mixture, as a replacement for the fatty substances removed from the skin by the ethanol, and, if necessary, other excipients and additives.

Humectants may be present, such as polyvalent alcohols, especially di- or triol, such as pentandiol, e.g. 1,2-pentandiol.

Also pH-regulators are possible, e.g. to maintain the pH preferably in an area from 4.5 to 6.0, more preferably from 4.8 to 5.5 at 20 to 25° C.

The pharmaceutical preparation for topical administration according to the invention can be prepared by mixing the aforementioned active ingredient with non-toxic, therapeutically inert, solid or liquid carriers customarily used in such preparations. These preparations preferably comprise 0.1 to 30 percent by weight, especially 0.1 to 10.0 percent by weight, preferably 0.3 to 8.0 percent by weight, of the active ingredient(s), based on the total weight of the compo-sition.

The surface active protein preferably is generally used (added)/present, according to the invention, in an amount from 0.001 to 5% of the weight of the pharmaceutical formulation, e.g. from 0.01 to 2%, such as from 0.02 to 1% or 1% to 5% by weight, respectively. Already very low amounts may be sufficient, showing the high penetration enhancing activity of the surface active proteins used/present according to the invention.

The remainder may be one or more pharmaceutically acceptable excipients e.g. as described above, including carrier material(s) and/or further additives.

The dosage to be applied depends on the position and the disease or disorder to be treated—for example, an amount of 0.1 to 50 mg may be applied once or several, e.g. up to three times a day, per $cm^2$ of area to be contacted. The dosage applied may also vary according to the species, size, sex, weight and other particular features of the patient to be treated.

The preparation (manufacture) of the topical pharmaceutical formulations comprises standard methods for obtaining such topical formulations, e.g. for mixing the ingredients. At least one surface active protein and at least one active ingredient are added to the mixture or mixed as such, meaning that not necessarily a further pharmaceutical carrier or excipient needs to be present, though also one or more such carrier materials or excipients may added to achieve the final product. The sequence of addition of the components is usually important, advantageous sequences being known or easily derivable for the skilled artisan.

Topical administration is e.g. to the nail.

SHORT DESCRIPTION OF FIGURES

FIG. 1: A, Relative enhancement of caffeine permeation through in vitro skin model; B, Absolute values of caffeine recovery in maintenance medium

| Abbreviations: | |
|---|---|
| w/w | percentage or amount given as weight by weight |
| v/v | percentage or amount by volume |
| w/v | percentage or amount in terms of weight per volume (identical with w/w if density of liquid phase is 1 g/ml) |

The following examples serve to illustrate the invention without limiting its scope.
Preparation of Hydrophobins
General Procedures**
Preparation of hydrophobins_/**

A class I hydrophobin from *Schizophyllum conmune* (SC3) and a class II hydrophobin from *Trichoderma reesei* (HFBII) were used for the purpose of the invention. The protein sequences for said hydrophobins were obtained from NCBI/Gene Bank: SC3: accession number P16933 (www.ncbi.nlm-.nih.gov/entrez/viewer.fcgi?db=protein&val=1710860);
HFB II: accession number CAA72636 (www.ncbi.nlm.nih-.gov/protein/1903325).

Amino acid sequences were translated into nucleic acid sequences. After optimisation of codon usage towards *E. coli*, the cDNAs were synthesized (Sloning BioTechnology, Pucheim, Germany). Hydrophobin nucleic acid sequences were cloned into a pET vector comprising T7-RNA-polymerase and transformed into the expression host *E. coli* BL21 by methods known in the art (Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.).

Fermentation of *E. coli* BL21 (DE3) transformed with expression vector comprising the optimised hydrophobin cDNA was performed in a 10 litre scale for 16 hours using ZYM-5052 medium (25 mM $Na_2HPO_4$, 25 mM $KH_2PO_4$, 50 mM $NH_4Cl$, 5 mM $Na_2SO_4$, 20 mM $MgSO_4$, 5 g/l glycerol, 0.5 g/l glucose, 2 g/l alpha-lactose monohydrate, 5 g/l yeast extract, and 10 g/l NZ-amines (purchased from Sigma)) in the presence of 100 µg/ml ampicillin or 25 µg/ml kanamycin, respectively. After harvest of the biomass the sedimented cells were frozen in liquid nitrogen and stored at −80° C. After treatment of thawed aliquots of sedimented cells by sonication, the released inclusion bodies were solubilised by boiling the cell homogenate for 30 sec. and stirring for 2 h at 600 rpm at 20° C.

Cell debris was sedimented by centrifugation for 10 min and the protein containing supernatant was passed through a filter with 0.22 µm. The filtrate was separated by affinity chromatography on nickel sepharose (GE Healthcare) and the eluted fractions were analysed on SDS polyacrylamide gel electrophoresis. The hydrophobin-containing fractions were cumulated and subsequently the hydrophobin-containing solution is desalted by dialysis in a Slide-A-Lyzer (Pierce) with a 10 kDa cut off membrane against water (30 ml eluate in 3 liters of water for 16 hours).

The protein concentration is determined using a BCA assay (Pierce). The hydrophobin solution was quick-frozen in liquid nitrogen and lyophilised.

EXAMPLE 1

Permeability Studies with Nails

Preparation of the Formulations and Buffer Solution

A formulation with one enhancer, Trichoderma reesei hydrophobin HFBII (isolation see Nakari-Setälä, T., Aro, N., Ilmen, M., Kalkkinen, N. and Penttilä, M. 1997, Differential expression of the vegetative and spore-bound hydrophobins of Tricoderma reesei, Cloning and characterization of the hfb2 gene. Eur. J. Biochem. 248, pp. 415-423) or H*A (His-tagged hydrophobin DewA fused to the solubility tag Yaad, supplied by BASF; for production see WO 2006/082251), and caffeine as model active ingredient and water was evaluated against a similar formulation containing 20% (v/v) ethanol in water instead of pure water. As ethanol is a potential solvent for substances poorly soluble in water and prevents from microbiological growth, a better or a similar permeability is desirable. For the permeability experiment, each enhancer was used in a formulation containing water as solvent and in parallel a formulation containing 20% (v/v) ethanol in water as solvent. The concentrations of the enhancers were 5% (w/v or v/v) except for docusate sodium salt with 1% (w/v) and hydrophobins with 0.02 and 0.1%, respectively. All formulations contained caffeine as a model active ingredient in a concentration of 2% (w/v). With this caffeine-concentration the solution was nearly saturated. This was intended to achieve a faster steady state according to the highest concentration gradient possible. Phosphate buffered saline (PBS) was prepared with a pH of 7.4. Both pH and osmolality of PBS simulated in the Franz diffusion cell's acceptor chamber the physiological conditions of blood (a systemic buffer system). The water used for the formulations and PBS was freshly produced, double distilled and filtered.

Permeation Studies

Healthy nails for the permeability experiments were obtained from the Institute of Anatomy of the University of Basel and from the Institute of Anatomy of the University of Freiburg, Germany. Franz Diffusion Cells (SES GmbH—Analysesysteme, Bechenheim, Germany) with a diffusion area of 0.785 cm² were used. The nails were completely hydrated by immersing them in PBS for one hour and then cut with a metal puncher, which had a diameter of 16 mm. Subsequently, they were mounted in the diffusion cells in an appropriate manner. The acceptor chamber below the nail was filled with 5 ml PBS. The formulation (400 µl) was applied onto the nail. In order to keep the temperature in the system constant, the glass cells were tempered by a water jacket kept at 32°. The acceptor chambers were stirred with a magnetic stirrer at 400 rpm. The openings for the formulations and extensions for taking samples were covered with Parafilm (film comprising paraffin wax and polyethene; American National Can Company, USA). A sample of 400 µl was taken from each cell twice a day and replaced with the same amount of PBS warmed to 32° C. After six days, the experiment was stopped. The concentrations of the samples were measured with UV-spectrophotometry. Flux and permeation coefficients were calculated with the values after 48 hours, as in this time a steady state was obtained.

TABLE 1

Results of nail permeation studies carried out in the presence of hydrophobins

| | DMSO | HFBII | | | H*A |
|---|---|---|---|---|---|
| | 4.6%[3] | 0.1% | 0.02% | (0.025%)* | 0.02% |
| EF in water[1] | 2.14 | 1.50 | 1.91 | (1.03) | 1.83 |
| EF in EtOH[2] | 3.25 | 3.29 | — | (2.45) | — |

[1]Enhancement factor (EF) in water (20 mg/mL caffeine)
[2]Enhancement factor (EF) in 20% (v/v) EtOH/water (20 mg/mL caffeine)
[3]Percentages are given in w/v
*experimental set-up was changed
Enhancement factors denote the promoted penetration of caffeine through the clamped nail-plate compared to control with pure water or 20% EtOH in water

EXAMPLE 1a

Permeability Studies with Nails

Another penetration study was made following the same experimental set-up as in example 1 except that Terbinafine was used as the active agent, and using a class I hydrophobin (hydrophobin C) as described further above.

Figure 2:
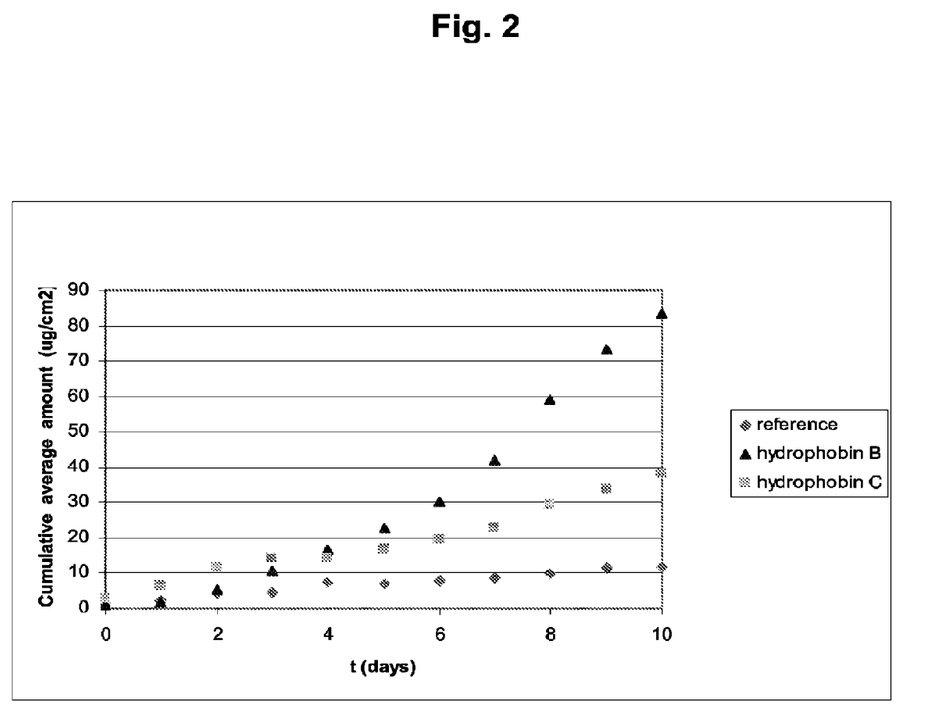
FIG. 2: Cumulative average amount of Terbinafine penetrated through nail (example 1a).

Formulations: 0.1% (w/v) hydrophobin+10% (w/v) Terbinafine in 60% (v/v) ethanol/water solution; reference is a solution of 10% (w/v) Terbinafine in 60% (v/v) ethanol/water. 3 sample treatments were averaged for each test. Results (shown in FIG. 2) document a clear enhancement by hydrophobin after 2-10 days of treatment (cumulated amounts after 10 days: ca. 83 mg/cm2, and ca 12 mg/cm2 using the reference solution only).

EXAMPLE 2

(Comparison): Permeability Studies with Skin

The penetration of caffeine through the skin was measured using a human epidermal skin model (EST-1000, Cell Systems, St. Katharinen, Germany). The in vitro model for human skin consists of a robust multilayer three-dimensional cell culture, which has been grown for 14 days and has skin-like properties. The cellular structure of EST-1000 resembles that of the natural epidermis showing a base membrane, proliferating keratinocytes and stratum corneum with an intact barrier function.

The tissues were provided in cell culture inserts with a polycarbonate membrane with 0.63 cm² surface area and 0.4 µm pore size. The membranes were covered completely by the cells and show a matte white, dry surface after complete differentiation. The inserts were handled easily by the use of a sterile forceps. Upon delivery, the skin inserts were equilibrated by placing each insert into a well of a 6-well cell culture dish containing 1 ml of maintenance medium (provided by Cell Systems). After 4-12 hours of equilibration the test substance was applied on the dry surface of the skin model. Penetration of substances applied onto the surface of the skin culture through the skin model was measured by sampling the medium surrounding the insert and detecting the concentration of the test substance, here caffeine.

For testing the ability of hydrophobin to enhance the permeability of caffeine through the skin the following experimental setup was chosen. Caffeine was purchased from Sigma and applied in a concentration of 10 mg/ml (1% w/v). SC3 is a hydrophobin of 112 amino acids from *Schizophyllum commune*, ATCC 44200 and HBF II (named HB F2 in the figures) is a hydrophobin of 86 amino acids from *Trichoderma reesei* (new name: *Hypocrea jecorina*) ATCC 90557.

Experimental Set-Up

Control: application of 50 μl 1% caffeine in 50% EtOH/PBS to untreated skin model.

Pre-coating: pre-treatment of skin culture with 50 μl 100 μg/ml SC3 or HBF II, respectively, for 60 minutes followed by removal of remaining hydrophobin solution and application of 50 μl 1% caffeine in 50% EtOH/PBS.

Mixture: application of a mixture of 100 μg/ml SC3 or HBF II, respectively, and 1% caffeine in 50% EtOH/PBS and application 50 μl of the mixture onto the skin model.

Figure 1:
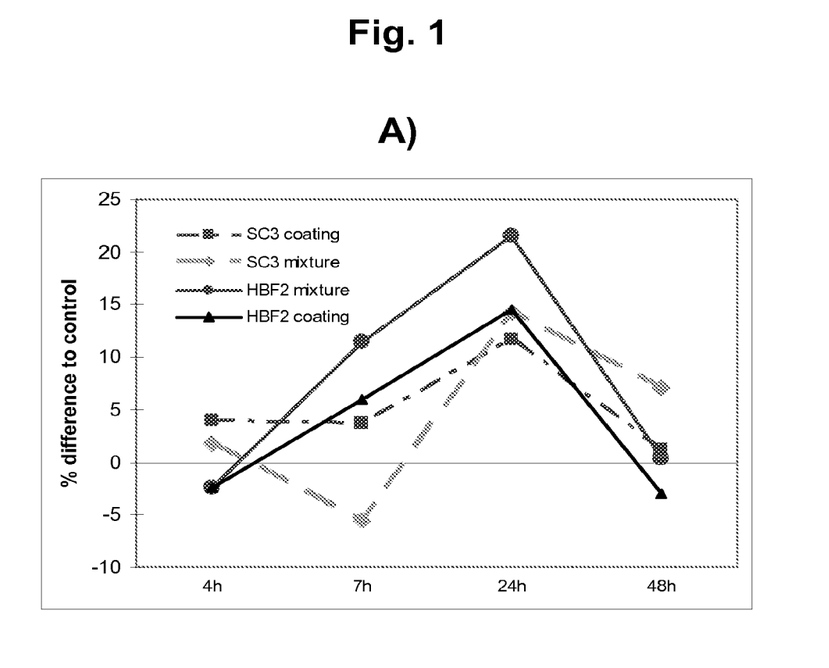
Figure 1B:
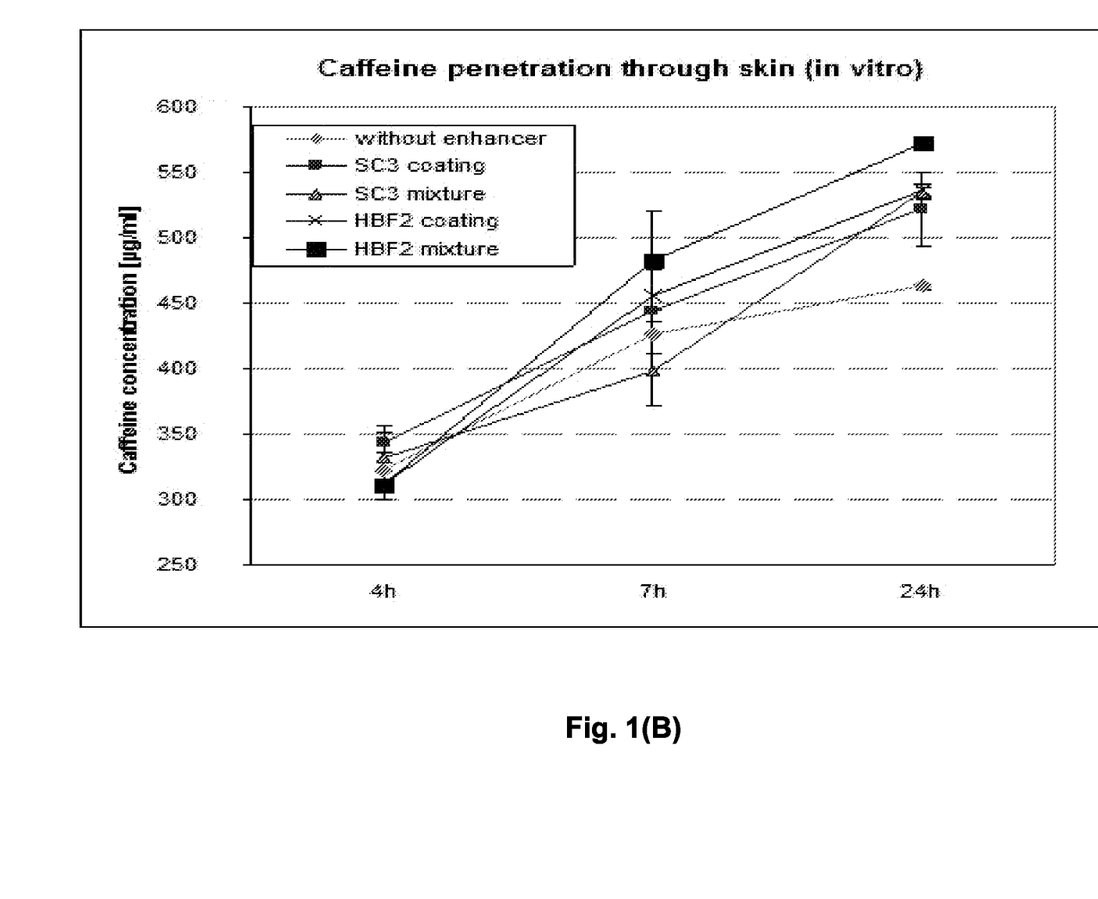

Within 48 hours of incubation in a cell culture incubator at 37° C. and 5% $CO_2$, 100 μl medium were sampled at different intervals (as given in table 2 and FIG. 1) from each well and the concentration of caffeine was determined by HPLC detection. Medium removed at each sampling was replaced by 100 μl fresh medium. Caffeine concentrations in the maintenance medium as shown in Table 2 are mean values of two independent skin cultures each.

Cytotoxicity of the test samples on the skin culture was determined by MTT-assay according to the instructions of the skin model provider. The viability of the cells in the skin model was not influenced by the solvents (50% ethanol, 0.002% SDS) as compared to cultures treated with PBS only. A viability of about 50% of that of the control cultures was observed when 1% caffeine or 1% caffeine/10 μg hydrophobin (SC3 or HFB II, respectively) were applied on the skin culture, showing that hydrophobin itself was not cytotoxic at a concentration of 200 μg/ml. The barrier function of the skin model is probably not influenced profoundly by the reduced viability of the cells, since the upper layer keratinocytes comprises non living cells. Furthermore, permeation enhancement was determined by comparison of skin cultures treated with 1% caffeine and cultures treated with 1% caffeine and 10 μg hydrophobin, both exhibiting the same viability as determined at the end of the experiment after 48 hours.

The results show that SC3 and HFB II both enhance the penetration of caffeine (1% w/v) through the in vitro model of human skin by up to 21.5% (Table 2). The mixture of hydrophobin with caffeine has a penetration enhancing effect superior to the pre-coating with hydrophobin and application of caffeine one hour after application of hydrophobin, which is advantageous for a potential formulation of a skin-effective drug in admixture with hydrophobin as permeation enhancer. The class II hydrophobin HFB II is slightly more effective in terms of permeation enhancement than class I hydrophobin SC3.

TABLE 2

Results of skin permeation studies carried out in the presence of hydrophobins

| | Hydrophobin | | | |
|---|---|---|---|---|
| | SC3 | | HFB II | |
| | Treatment | | | |
| | Precoating | Mixture | Precoating | Mixture |
| Enhancement* | 11.70 | 14.21 | 14.55 | 21.55 |

TABLE 2-continued

Results of skin permeation studies carried out in the presence of hydrophobins

| | Hydrophobin | | | |
|---|---|---|---|---|
| | SC3 | | HFB II | |
| | Treatment | | | |
| | Precoating | Mixture | Precoating | Mixture |
| after 24 h | | | | |

*Enhancement: % increase of caffeine (20 mg/ml) penetration as compared to control without hydrophobin See also FIG. 1A and FIG. 1B which show more details.

The invention claimed is:

1. A method of enhancing transungual delivery of at least one pharmaceutically active ingredient through a nail of a patient, said method comprising providing a surface active protein in a pharmaceutical formulation together with the at least one pharmaceutically active ingredient, and topically administering the pharmaceutical formulation to said nail of the patient, thereby delivering the at least one pharmaceutically active ingredient transungually to the patient.

2. The method of claim 1, wherein, the surface active protein is present in a range from about 0.001 to 5%, based on the weight of the pharmaceutical formulation.

3. The method according to claim 1, where the surface active protein is one or more proteins selected from the group consisting of latherin, Phospholipase C, amyloid or amyloid-like proteins, alasan, SapB, glycolipid transfer protein and a chapline or is a protein or mixture of proteins selected from the group consisting of hydrophobins.

4. The method according to claim 1, where the surface active protein is one or more proteins selected from natural hydrophobins and recombinant hydrophobins, which may be unmodified or glycosylated, acylated or cross-linked.

5. The method according to claim 1, where the surface active protein is one or more polypeptides of formula (I)

$$X_n\text{-}C^1\text{-}X_{1\text{-}50}\text{-}C^2\text{-}X_{0\text{-}5}\text{-}C^3\text{-}X_{1\text{-}100}\text{-}C^4\text{-}X_{1\text{-}100}\text{-}C^5\text{-}X_{1\text{-}50}\text{-}C^6\text{-}X_{0\text{-}5}\text{-}C^7\text{-}X_{1\text{-}50}\text{-}C^8\text{-}X_m \quad (I)$$

wherein X can be any of the 20 naturally occurring amino acids Phe, Leu, Ser, Tyr, Cys, Trp, Pro, His, Gln, Arg, Ile, Met, Thr, Asn, Lys, Val, Ala, Asp, Glu or Gly, the X's can be the same or different, the indices adjacent to X in each case indicate the number of amino acids, $C^1$-$C^8$ are cysteine, alanine, serine, glycine, methionine or threonine, at least four of $C^1$-$C^8$ are cysteine, and the indices n and m, each independently of the other, are natural numbers from 0 to 500.

6. The method according to claim 5, where the amino acids designated $C^1$ to $C^8$ are cysteine.

7. The method according to claim 1, where the surface active protein is a protein or mixture of proteins selected from the group consisting of class I hydrophobins and class II hydrophobins.

8. The method according to claim 7, where the class I hydrophobins are CFTH1, SC4, ABH3, EAS or SC3 from *Schizophyllum commune* and the class II hydrophobins are HFBII, HFBI, SRHI, QID3, TRI1, TRI2, TRI3, the three segments of TH1, CPPHI__1, CPPH1__2, CPPH__3, CPPH__4, CPPH__5, the five segments of cpphl, CRYPA, CU, MAG, HCF5 or HCF6.

9. The method according to claim 1, where the at least one pharmaceutically active ingredient is selected from the group consisting of antibiotics, antiphlogistics, anti-rheumatics, analgesics, antipyretics, anti-inflammatory ingredients, keratolytics, antiproliferative agents, therapeutics or prophylactics against acne and agents against endogenous or exogenous eczema.

10. The method according to claim 1, where the surface active protein has the property at room temperature, after coating a glass surface, to bring about an increase in the contact angle of a water droplet of at least 20°, by comparison with the contact angle of a water droplet of the same size with the glass surface uncoated.

* * * * *